United States Patent [19]
Matthijs et al.

[11] Patent Number: 5,407,422
[45] Date of Patent: Apr. 18, 1995

[54] PELVIC BELT

[75] Inventors: Omer Matthijs; Valerie Phelps, both of Tucson, Ariz.

[73] Assignee: Sharon C. Hanson, Plymouth, Minn.

[21] Appl. No.: 317,893

[22] Filed: Oct. 4, 1994

[51] Int. Cl.$^6$ .............................. A61F 5/37; A61F 5/02
[52] U.S. Cl. ...................................... 602/19; 128/876; 2/338
[58] Field of Search ....... 128/869, 875, 876, DIG. 15; 602/19; 2/310, 311, 312, 338; 24/170, 180, 121

[56] References Cited

U.S. PATENT DOCUMENTS

| | | | |
|---|---|---|---|
| 3,374,636 | 3/1968 | Mason | 2/312 |
| 4,964,401 | 10/1990 | Taigen | 128/876 |
| 5,036,864 | 8/1991 | Yewer | 128/876 |
| 5,070,866 | 12/1991 | Alexander | 128/876 |
| 5,086,758 | 2/1992 | Schick | 128/876 |
| 5,178,163 | 1/1993 | Yewer | 128/876 |
| 5,267,947 | 12/1993 | James | 602/19 |
| 5,269,050 | 12/1993 | Yewer | 128/876 |
| 5,309,926 | 5/1994 | Mayton | 128/876 |
| 5,316,022 | 5/1994 | Schiek | 128/826 |

*Primary Examiner*—Michael A. Brown
*Attorney, Agent, or Firm*—Palmatier, Sjoquist & Helget

[57] ABSTRACT

A pelvic belt may be used in the treatment of instability in the SI joint or pubic symphysis region for an individual. The use of a pelvic belt reduces the ability of the innominate bones of an individual to be pushed outwardly from each other during movement. The pelvic belt includes a first portion having an attachment means for fastening the belt about the pelvic ring at a height approximately aligned to the base of the wedge between the sacrum and ilium bones, or just above the greater trochanter region, for an individual. The pelvic belt also includes a second portion, a third portion and a fourth portion. The second and fourth portions include an area having an increased surface dimension with respect to the first and third portions. Additionally, the second and fourth portions include an interior non-slip surface to facilitate the retention of the pelvic belt in a desired position about the pelvic ring of an individual. A fifth portion extends from the fourth portion, where the fifth portion includes a clasping loop for engagement to the first portion during the affixation of the pelvic belt to an individual.

8 Claims, 3 Drawing Sheets

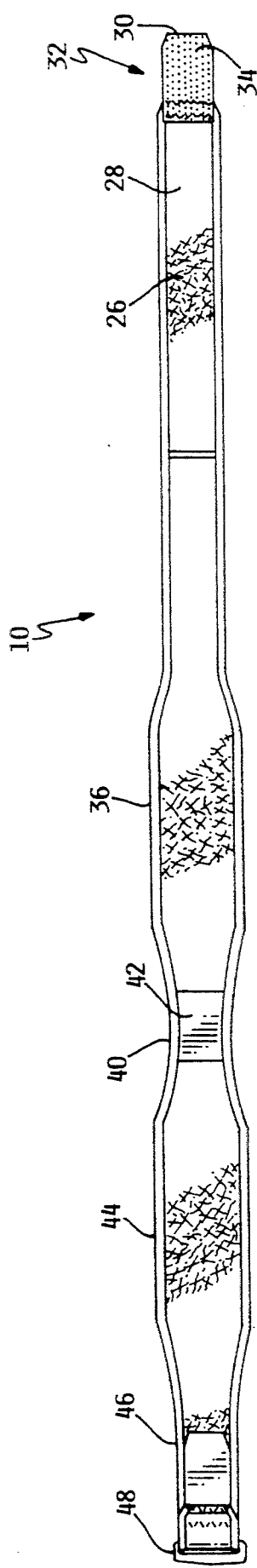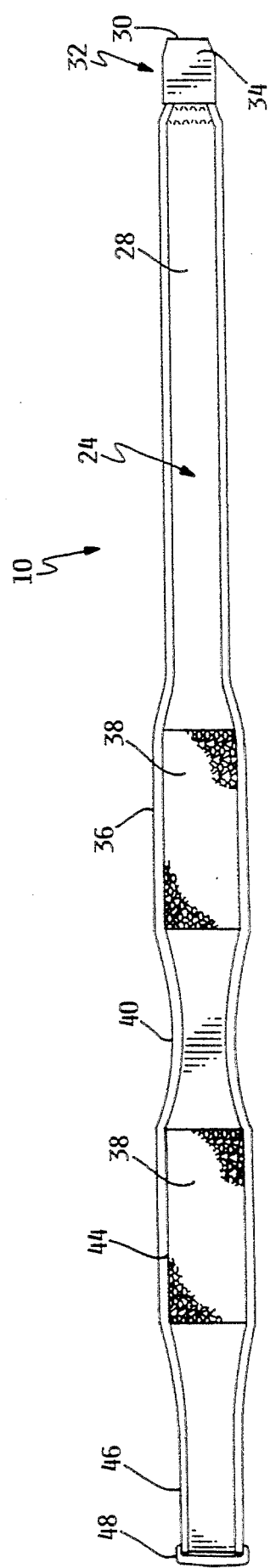
FIG. 4
FIG. 5

PELVIC BELT

BACKGROUND OF THE INVENTION

The pelvic region of an individual generally consists of the left and right ilium and the sacrum. The sacrum articulates with both the left and right ilium via the left and right sacroiliac joints. Both the left and right ilium are connected mutually to each other through the pubic symphysis or SI joint by a sacroiliac joint cartilage. This entire complex may be referred to as the "pelvic ring."10 The sacroiliac joint cartilage is different from cartilage found in other parts of the body. The structural development of the cartilage in the sacroiliac joint is not the same as in the other joints of the body. First of all, the normal smooth hyaline cartilage is absent. From the end of puberty on, the cartilaginous covering of the sacrum is relatively soft and thick. Microscopically, the sacroiliac cartilage, especially of the ilium, develops a rougher tissue than cartilage in other synovial joints. Secondly, macroscopic ridges develop on the sacroiliac joint cartilage surfaces along with complementary grooves on the opposite joint surfaces. This combination of microscopic roughness as well as macroscopic ridges and grooves provides the SI joint with more springing stability than motion.

In the frontal plane of the pelvic ring, the SI joint surfaces converge caudally. This converging position of both joint surfaces is beneficial in supporting body weight. On the other hand, the sacrum has a wedge form and is driven by the load of the spinal column between the two innominate bones, which in effect pushes the bones outwardly from each other.

The lumbar spine, pelvic ring and hip joints of an individual form a functional unit. Almost every movement of the lumbar spine has an influence on the pubic symphysis and both SI joints. The movements of an individual generate forces which are transferred through the sacrum and SI joints which are communicated or transferred to the hip joints and then to the remaining parts of an individual's lower extremities. In some individuals, movement may cause the load of the spinal column to push the two innominate bones outwardly, and when the ligaments are intact this will have a self-bracing stabilizing effect. If, however, the ligaments are lax, the self-bracing system will be less effective and then instability will occur.

Women, following childbirth, and other individuals may suffer from instability of the sacrum-ilium joint or (SI joint) or pubic symphysis. The instability of the SI joint or pubic symphysis may be treated over a period of time through muscle strengthening activities usually associated with a daily exercise program such as walking. In general, an individual through exercise attempts to strengthen the gluteus maximus muscle which is individually attached to the sacrum as well as to the ilium. In addition, a stabilizer belt for the SI joints and/or the pubic symphysis is beneficial for reduction of instability of the sacrum-ilium joint. No such belt is known which prevents the innominate bones from outward separation from each other, which in turn facilitates the alignment of the grooves and ridges of the sacrum-ilium joint surfaces for firm engagement to each other. The enhanced engagement of the grooves and ridges significantly reduces the rehabilitative time required to cure instability of the sacrum-ilium joint.

SUMMARY OF THE INVENTION

A pelvic belt may be used in the treatment of instability in the SI joint or pubic symphysis region for an individual. The use of a pelvic belt reduces the ability of the innominate bones of an individual to be pushed outwardly from each other during movement. The pelvic belt includes a first portion having an attachment means for fastening the belt about the pelvic ring at a height approximately aligned to the base of the wedge between the sacrum and ilium bones, or just above the greater trochanter region, for an individual. The pelvic belt also includes a second portion, a third portion and a fourth portion. The second and fourth portions include an area having an increased surface dimension with respect to the first and third portions. Additionally, the second and fourth portions include an interior non-slip surface to facilitate the retention of the pelvic belt in a desired position about the pelvic ring of an individual. A fifth portion extends from the fourth portion, where the fifth portion includes a clasping loop for engagement to the first portion during the affixation of the pelvic belt to an individual.

It is a principal object of the present invention to provide a new and improved pelvic belt of relatively simple and inexpensive design, construction and operation, which is safe and durable and which may be used by an individual during rehabilitation or treatment of SI joint or pubic symphysis instability without fear of further injuries to the person.

Another principal object of the present invention is to reduce and/or prevent the innominate bones of an individual from being pushed outwardly from each other during movement or exercise by the person.

It is still another object of the present invention to evenly disperse pressure around the pelvic ring of an individual during use of the belt to increase comfort and functional effectiveness during treatment of SI joint or pubic symphysis instability.

It is another object of the present invention to provide a lightweight and breathable pelvic belt for maximization of the comfort to an individual.

It is another principal object of the present invention to diminish or eliminate skin irritation resulting from use of the pelvic belt by an individual.

A feature of the present invention is a first portion having an attachment means for securing the pelvic belt about the pelvic region of an individual.

Another feature of the present invention is a second portion having a greater surface area or width as compared to the first portion for positioning proximate to an innominate bone of an individual.

Still another feature of the present invention is a non-allergenic, non-slip material integral to the interior surface of the second portion for retention of the pelvic belt in a desired position about the pelvic ring of an individual.

Still another feature of the present invention is a third portion having a reduced surface area or width as compared to the second portion, and an indicator tab for alignment to the sacrum of an individual.

Still another feature of the present invention is a fourth portion having a surface area approximately equal to the second portion.

Still another feature of the present invention is another section of non-allergenic, non-slip material integral to the interior surface of the fourth portion for positioning proximate to the other innominate bone of an individual.

Still another feature of the present invention is a fifth portion having a clasping loop for engagement to the attachment means during placement of the pelvic belt about the pelvic ring of an individual.

BRIEF DESCRIPTION OF THE DRAWINGS

FIG. 4 is an exterior view of the pelvic belt;

FIG. 5 is an interior view of the pelvic belt; and

DETAILED SPECIFICATION OF THE PREFERRED EMBODIMENT

One form of the invention is illustrated and described herein. In general, the pelvic belt is indicated by the numeral 10. The pelvic belt 10 is generally worn for rehabilitation or treatment of instability of the pubic symphysis 12 which may occur during or following pregnancy, or in cases of chronic hip abduction problems for an individual. As preventative measure after pregnancy, especially when performing strenuous activities, an individual may receive beneficial effects from wearing the pelvic belt 10. During pregnancy, the mobility of the sacrum-ilium joint (SI joint) increases due to hormonal changes. This increase in mobility may result in some reduced stability to the SI joint which may in turn cause back pain both during and after pregnancy. In addition, the pelvic belt 10 may be used to provide therapeutic and rehabilitative affects following the fracture of the pelvic ring.

Figure 6:
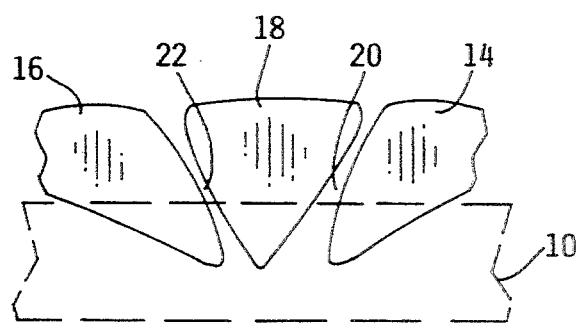
FIG. 6 is a detail view of the sacrum, ilium joint showing the positioning of the pelvic belt in phantom line.
Figure 2:
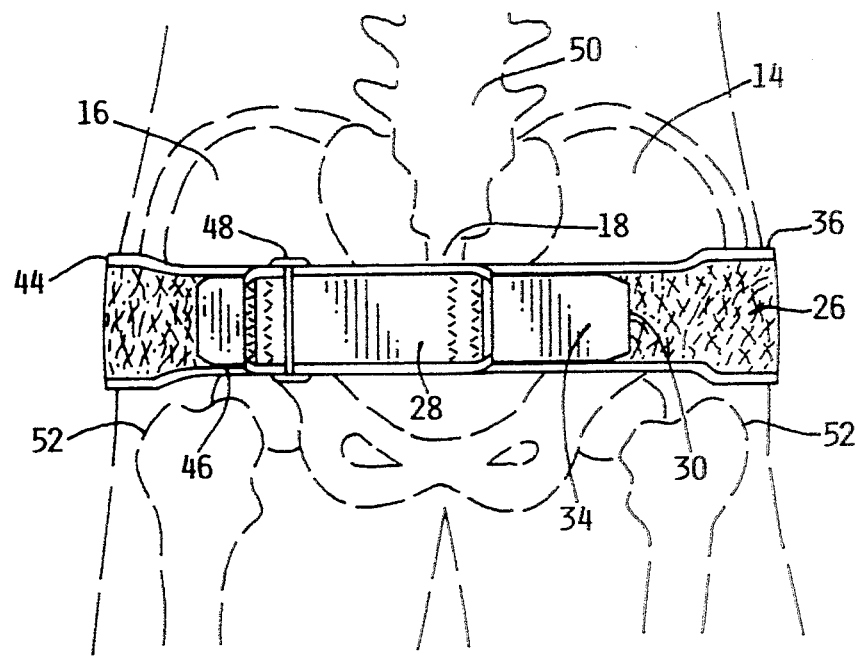
FIG. 2 is a front environmental partial phantom view of the pelvic belt surrounding the pelvic ring of an individual.
Figure 3:
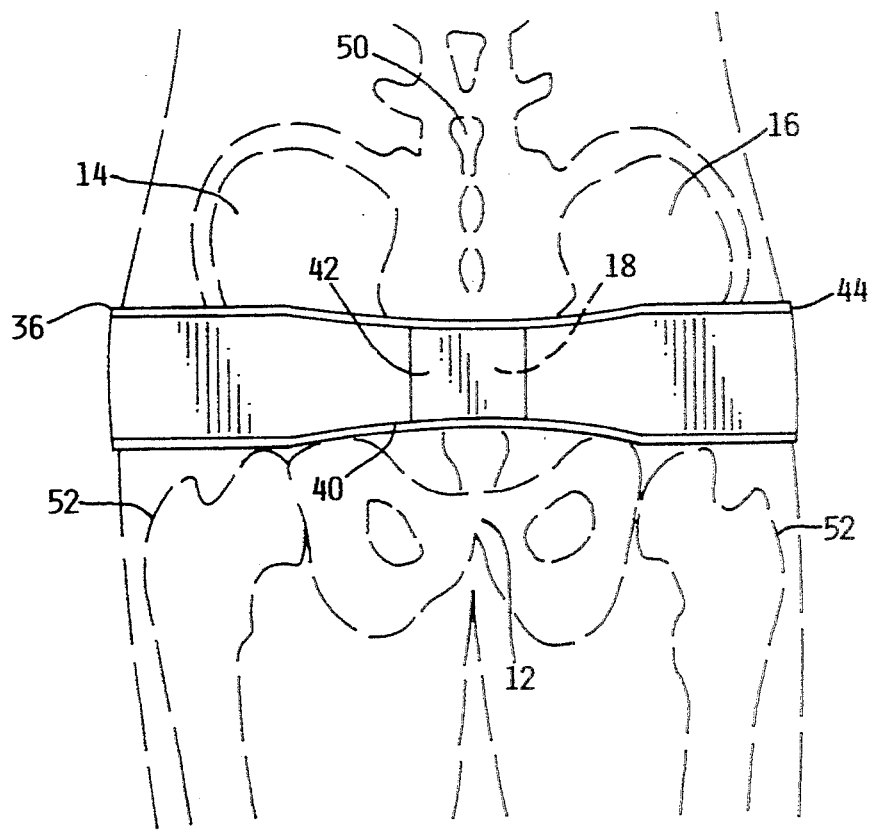
FIG. 3 is a rear environmental, partial phantom line view of the pelvic belt surrounding the pelvic ring of an individual.

In general, the pelvic region of an individual can be divided into three parts which include the left ilium 14, the right ilium 16 and the sacrum 18. In general, the sacrum 18 articulates with both the left and right ilium 14, 16 by means of a left sacroiliac joint 20 and right sacroiliac joint 22. Both left and right ilium 14, 16 are connected mutually to each other through the pubic symphysis 12. The entire complex is sometimes referred to as the pelvic ring (FIGS. 2, 3 and 6).

In general, the pelvic belt includes an interior surface 24 and an exterior surface 26. The pelvic belt 10 is preferably formed of a lightweight and breathable material in order to maximize the comfort to an individual during use.

Figure 1:
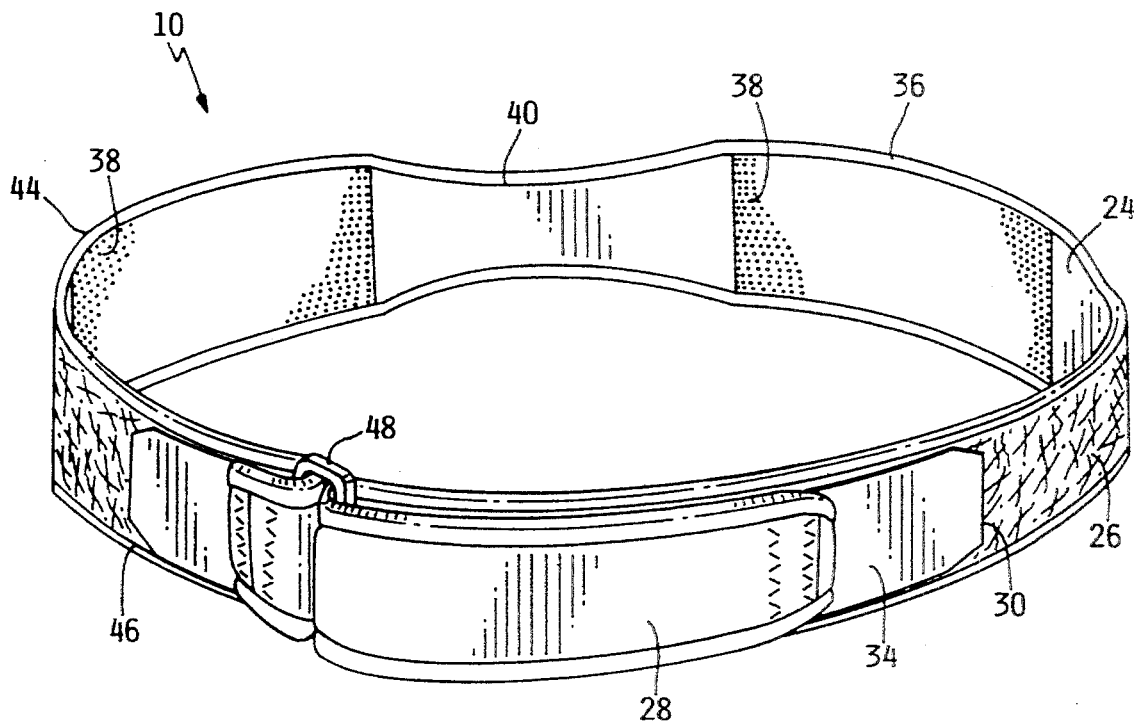
FIG. 1 is an isometric view of the pelvic belt.

The pelvic belt 10 includes a first portion 28. A means for attachment 32 is preferably engaged to the first end 30 of the first portion 28. In the preferred embodiment, the means for attachment 32 is formed of an affixation member 34 which contains a plurality of hooks adapted for engagement to loop material which is either integral with, or attached to, the exterior surface 26 of the first portion 28. Alternatively, the means for attachment 32 may be a buckle at the preference of an individual provided that the essential features, functions and attributes described herein are not sacrificed. It should be noted that any means for attachment 32 may be used in conjunction with the pelvic belt 10 during application about the pelvic ring of an individual (FIGS. 1, 4 and 5).

The first portion 28 preferably includes a uniformly-sized surface area or width which facilitates the engagement of the means for attachment 32 to the exterior surface 26. The first portion 28 may also be pliable and adapted for foldable positioning adjacent to itself during the affixation of the pelvic belt 10 around the pelvic ring of an individual. It should be noted that the first portion 28 is preferably of sufficient length to permit the means for attachment 32 to be affixed to the exterior surface 26 of the first portion 28.

A second portion 36 preferably extends from the first portion 28. The second portion 36 preferably includes a uniformly sized surface area or width having increased dimensions with respect to the surface area or width of the first portion 28 (FIGS. 1, 4 and 5).

In the preferred embodiment a non-slip and non-allergenic material 38 is preferably integral to the interior surface 24 adjacent to the second portion 36. The non-slip material 38 may completely cover the interior surface 24 of the second portion 36 at the discretion of an individual. The non-slip material 38 may be attached to the interior surface 24 by any means preferred by an individual including but not limited to the use of stitching.

The non-slip material 38 and the second portion 36 are preferably adapted for positioning proximate to either the left or right ilium bones 14, 16 of an individual. The increased surface area or width of the second portion 36 functions to provide enhanced retention properties of the pelvic belt 10 in a desired position when engaged to the pelvic ring. The increased surface area or width of the second portion 36 additionally enhances the dispersement of pressure around the pelvic ring while simultaneously minimizing separation of the left or right innominate bones or left or right ilium bones 14, 16 from the sacrum 18.

A third portion 40 preferably extends from the second portion 36. The third portion 40 preferably has a uniform surface area or width of reduced dimensions as compared to the second portion 36. In the preferred embodiment, the surface area or width of the third portion 40 is approximately equal to the surface area or width of the first portion 28 (FIGS. 1, 4 and 5).

The exterior surface 26 of the third portion 40 preferably includes an indicator tab 42, which may be used by an individual for alignment to the middle of the individual's sacrum 18. The indicator tab 42 functions to enhance an individual's ability to properly align the pelvic belt 10 around the pelvic ring. The indicator tab 42 is preferably centrally positioned with respect to the sacrum 18, which in turn properly positions the second portion 36 proximate to either the left or right ilium bones 14, 16 of the individual.

A fourth portion 44 preferably extends from the third portion 40. The fourth portion 44 preferably has a uniform surface area or width having an increased size dimension which is approximately equal to the surface area or width of the second portion 36. Another section of non-slip/non-allergenic material 38 is preferably integral to the interior surface 24 adjacent to the fourth portion 44. The non-slip material 38 may completely cover the interior surface 24 of the fourth portion 44 for positioning proximate either to the left ilium 14 or left innominate bone of an individual. The increased surface area dimension or width of the fourth portion 44 preferably facilitates the retention of the pelvic belt 10 in a desired position when engaged to the pelvic ring of an individual (FIGS. 1, 4 and 5).

In the preferred embodiment, the non-slip material 38 is preferably attached to fourth portion 44 by the same means used to attach the non-slip material 38 to the second portion 36. The non-slip material 38 may be formed of any resiliently pliable non-allergic rubber or plastic material as preferred by an individual which permits the second portion 36 and/or and the fourth portion 44 to conform to the contours of the pelvic ring of an individual.

The second portion 36 and the fourth portion 44 are preferably spaced from each other and are of sufficient length for flush surrounding engagement of either the left or right ilium 14, 16 or left or right innominate bones of an individual. It should also be noted that third portion 40 is preferably of sufficient length to permit the positioning of the second portion 36 and fourth portion 44 opposite to each other when the pelvic belt 10 is positioned around the pelvic ring of an individual.

A fifth portion 46 preferably extends from the fourth portion 44. The fifth portion 46 preferably has a uniform surface area or width having a reduced dimension as compared to the fourth portion 44. The surface area or width of the fifth portion 46 is approximately equal to the surface area or width of the third portion 40 or the first portion 28.

The fifth portion 46 preferably includes a clasping loop 48 which is adapted for receiving engagement of the means of attachment 32 or the affixation member 34. (FIG. 1) During use of the pelvic belt 10, the affixation member 34 is preferably slidably positioned through the clasping loop 48 following positioning of the pelvic belt 10 proximate to the pelvic ring of the individual. The affixation member 34 and the first portion 28 may then be drawn through the clasping loop 48 for the snug positioning around the pelvic ring of an individual.

In an alternate embodiment, the clasping loop 48 may include a tongue member for engagement to a buckle of the means for attachment 32 for securely positioning the pelvic belt 10 to an individual.

The lumbar spine 50, the pelvic ring and the hip joints of an individual form a functional unit. Almost every movement of the lumbar spine 50 has an influence on the pelvic joints which consist of both SI joints and the pubic symphysis 12.

During use, the pelvic belt 10 prevents the innominate bones or left and right ilium 14, 16 from being pushed away from each other, therefore retaining the grooves and ridges of the joint surfaces more firmly into contact with each other. The increased surface area or width of the second portion 36 and fourth portion 44, as positioned proximate to the left and right ilium 14, 16 of an individual, disperse pressure more evenly about an individual's pelvic ring. The comfort and functional effectiveness of the pelvic belt 10 is thereby significantly increased. The non-allergenic, non-slip material 38 significantly diminishes any skin irritation to an individual which may occur through use of the pelvic belt 10.

The pelvic belt 10 may be placed in surrounding relationship about the pelvic ring of an individual during standing. However, the best results for engagement of the pelvic belt 10 to the pelvic ring are achieved when the pelvic belt 10 is applied while an individual is lying supine on a bed, floor or other firm surface. The pelvic belt 10 is preferably worn at a level directly above the most cranial aspect of the greater trochanters 52. The indicator tab 42 may then be aligned with the midline of an individual's sacrum 18. According to a patient's preference, the means for attachment 32 may be worn asymmetrically at the front of the lower pelvis, on either the left or right side, or symmetrically in the middle. In general, the force necessary to obtain stabilization and alleviate pelvic instability ranges from eighteen to thirty-three pounds. The pelvic belt 10 is preferably worn over the undergarments of an individual in order to minimize risk of skin irritation which may occur due to small shifts of the belt during use.

As may be seen in FIG. 6 the pelvic belt 10 is preferably positioned around the pelvic ring of an individual at the base of the wedge between the sacrum 18 and left and right ilium 14, 16 respectively. The pelvic belt 10 should not be positioned proximate to the top of the wedge between the sacrum 18 and the left and right ilium 14, 16 respectively. The application of the pelvic belt 10 just above the greater trochanters 52 prevents the opening of the gap in the SI joint or the downward positioning of the SI joint below the pelvic belt 10. Proper positioning of the pelvic belt 10 prevents the innominate bones or left and right ilium 14, 16 from being pushed outwardly from each other which in turn retains the grooves and ridges of the SI joint surfaces more firmly into contact with each other significantly facilitating the stability and the healing of the SI joints.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

What is claimed is:

1. A pelvic belt for engagement around the pelvic ring of an individual, said pelvic belt comprising:
   (a) a first portion having a first end having a first surface area, said first portion further having a means for attachment;
   (b) a second portion having a second surface area of increased dimension with respect to said first surface area, said second portion having an interior surface having a non-slip material engaged thereto;
   (c) a third portion having a surface area approximately equal to said first surface area, said third portion having a centrally-positioned indicator tab for alignment to the sacrum of said individual;
   (d) a fourth portion having a surface area approximately equal to said second surface area, said fourth portion having an interior surface having a non-slip material engaged thereto; and
   (e) a fifth portion having a second end having a clasping loop for engagement to said means for attachment.

2. The pelvic belt according to claim 1, said first portion, said second portion, said third portion, said fourth portion and said fifth portion comprising an exterior surface.

3. The pelvic belt according to claim 2, said exterior surface comprising loop material for engagement to said attachment means.

4. The pelvic belt according to claim 1, said means for attachment comprising an affixation member comprising hook material.

5. The pelvic belt according to claim 1, said means for attachment comprising a buckle.

6. The pelvic belt according to claim 5, said clasping loop further comprising a tongue member for engagement to said buckle.

7. The pelvic belt according to claim 1, wherein said second portion and said fourth portion are spaced from each other for engagement to said individual proximate to the innominate bones of said individual.

8. A pelvic belt for engagement around the pelvic ring of an individual, said pelvic belt comprising:
   (a) a first portion having a first end having a first surface area, said first portion having an affixation member comprising hook material, said first portion further having an exterior surface having loop material for engagement to said affixation member;
   (b) a second portion having a second surface area of increased dimension with respect to said first surface area, said second portion having an interior surface having a non-slip material engaged thereto for reducing rotation of said pelvic belt about said pelvic ring of said individual, said second portion being adjacent to said first portion;
   (c) a third portion having a third surface area approximately equal to said first surface area, said third portion having a centrally-positioned indicator tab for alignment to the sacrum of said individual, said third portion being adjacent to said second portion;
   (d) a fourth portion having a fourth surface area approximately equal to said second surface area, said fourth portion having an interior surface having a non-slip material engaged thereto for reducing rotation of said pelvic belt about said pelvic ring of said individual, said fourth portion being adjacent to said third portion, said fourth portion being spaced from said second portion for engagement of said second portion and said fourth portion proximate to the innominate bones of said individual where said second portion and said fourth portion are positioned opposite to each other; and
   (e) a fifth portion having a second end having a clasping loop for engagement to said affixation member during engagement of said hook material to said loop material during attachment of said pelvic belt about said pelvic ring of said individual.

* * * * *